United States Patent [19]

Steer

[11] Patent Number: 4,795,435

[45] Date of Patent: Jan. 3, 1989

[54] DEVICE FOR PROTECTING A WOUND

[75] Inventor: Peter L. Steer, Surrey, England

[73] Assignee: E. R. Squibb & Sons, Inc., Princeton, N.J.

[21] Appl. No.: 578,163

[22] Filed: Feb. 8, 1984

[30] Foreign Application Priority Data

Feb. 25, 1983 [GB] United Kingdom ............... 8305234
Mar. 18, 1983 [GB] United Kingdom ............... 8307529
May 5, 1983 [GB] United Kingdom ............... 8312335

[51] Int. Cl.[4] .................................................. A61F 5/44
[52] U.S. Cl. ........................................ 604/355; 604/332; 128/760
[58] Field of Search ............... 424/19, 28; 128/760, 128/132 D, 155, 157; 604/360, 332–345, 355

[56] References Cited

U.S. PATENT DOCUMENTS

| | | | |
|---|---|---|---|
| Re. 29,319 | 7/1977 | Nordby et al. | 128/275 |
| 3,339,546 | 9/1967 | Chen et al. | 424/28 |
| 3,568,675 | 3/1971 | Harvey | 128/275 |
| 3,874,387 | 4/1975 | Barbieri | 128/325 |
| 4,023,569 | 5/1977 | Warnecke et al. | 128/154 |
| 4,224,941 | 9/1980 | Stivala | 128/207.26 |
| 4,250,882 | 2/1981 | Adair | 604/335 |
| 4,387,713 | 6/1983 | Calanni | 604/335 |
| 4,468,227 | 8/1984 | Jensen | 604/327 |
| 4,540,415 | 9/1985 | Kovpman | 604/390 |

FOREIGN PATENT DOCUMENTS

| | | |
|---|---|---|
| 366347 | 4/1931 | United Kingdom . |
| 540867 | 11/1941 | United Kingdom . |
| 606248 | 8/1948 | United Kingdom . |
| 1150294 | 4/1969 | United Kingdom . |
| 1549756 | 8/1979 | United Kingdom . |
| 2099308 | 12/1982 | United Kingdom . |

*Primary Examiner*—C. Fred Rosenbaum
*Assistant Examiner*—J. L. Kruter
*Attorney, Agent, or Firm*—Lawrence S. Levinson; Stephen B. Davis

[57] ABSTRACT

A device for wound management permits the application of an apertured pad to the wound and involves the provision of a protective compartment, optionally drained, whose interior is open to the wound and which is normally sealed closed but which can be opened if desired.

4 Claims, 2 Drawing Sheets

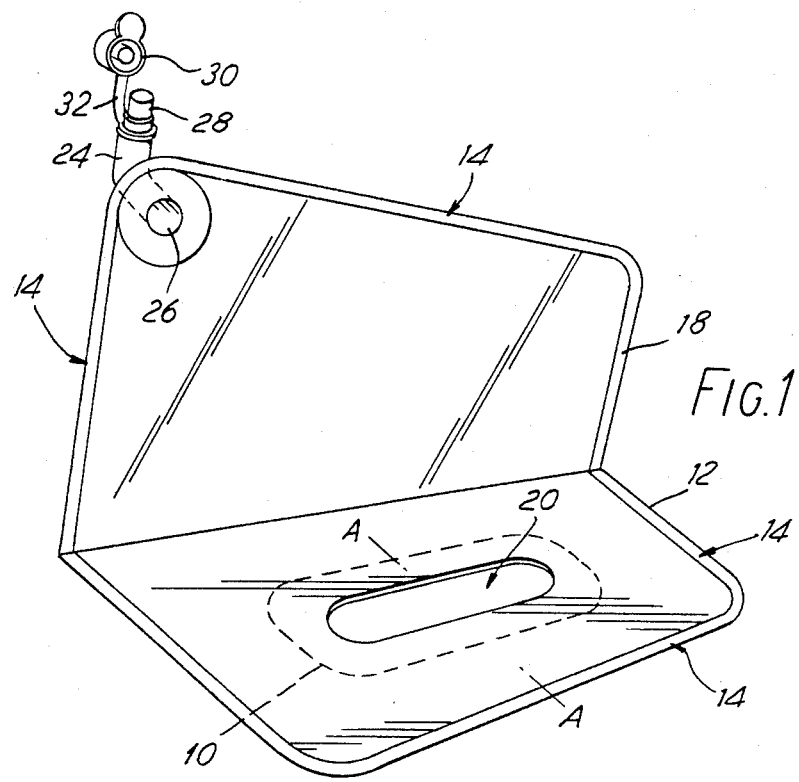
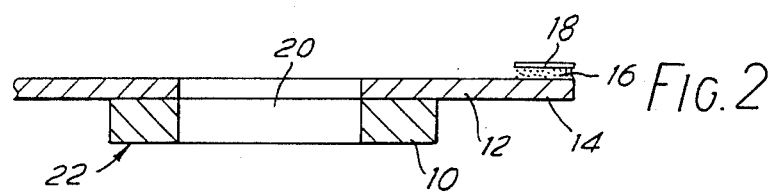
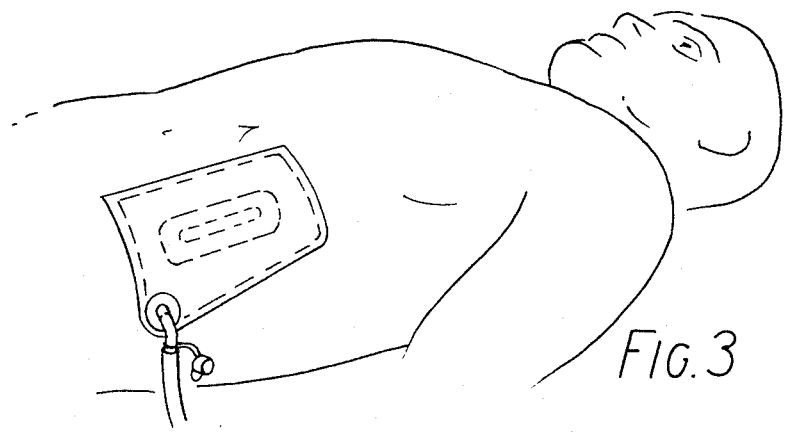

DEVICE FOR PROTECTING A WOUND

BACKGROUND OF THE INVENTION

Westaby et al. in British Pat. No. 1,549,756 disclose a wound irrigating device that includes a cover and a rim with a layer of adhesive on the rim for attaching the device to moist body surfaces. Such a device is appropriate for use with a wound of a specific size, or a specific range of sizes, and hence a hospital is obliged to hold a stock of devices to cater for different patients. Also, there are difficulties in arranging for continuous drainage of wounds, e.g., resulting from surgery, which are so protected.

Jensen in U.K. Patent Application No. 2,099,308 discloses a wound drainage device in the form of a flexible pouch having top and bottom walls and pleated side walls that allow the top wall to be lifted a limited distance without transmitting appreciable lifting forces to the bottom wall when the bottom wall is surgically apertured and secured about a wound sight. The top wall includes an access opening having a flanged locking ring of flexible plastics extending thereabout. A removable closure cap is attached to the access opening, the cap having a flat rim of flexible plastics with circumferential locking ribs releasably and sealingly engaging a series of mating ribs provided by the flanged portion of the ring.

Nordby et al. in U.S. Pat. No. Re. 29,319 disclose a wound drainage system which includes a drainable pouch having an apertured wall provided with an annular adhesive patch for securing the pouch to a patient in an area surrounding the wound site. The opposite wall of the pouch is provided with an access opening, and a transparent cap is adhesively secured to the pouch about that opening. When access to the wound is required for surgical examination, drain adjustment, wound treatment, or any other reason, the pressure-sensitive adhesive seal between the cap and pouch is broken and the cap is temporarily removed.

Other wound drainage and treatment devices are disclosed by Harvey in U.S. Pat. No. 3,568,675, Barbieri in U.S. Pat. No. 3,874,387, Warnecke et al. in U.S. Pat. No. 4,023,569, Stivala in U.S. Pat. No. 4,224,941, Adair in U.S. Pat. No. 4,250,882, Sander in British Pat. No. 366,347, Kendall in British Pat. No. 540,867, Smith in British Pat. No. 606,248, and General Electric Co. in British Pat. No. 1,150,294.

SUMMARY OF THE INVENTION

According to the invention in its broadest aspect there is provided a device for wound management which permits the application of an apertured pad to the wound and involves the provision of a protective compartment, optionally drained, whose interior is open to the wound and which is normally sealed closed but which can be opened if desired.

According to one embodiment of the invention, there is provided a device for protecting a wound comprising a pad of skin-protective and skin-curative adhesive material to which is secured a foldable sheet of liquid-impermeable material of larger area than the pad. Marginal areas of the sheet are provided with a sealing means and the sheet is located and dimensioned so that the sheet when folded over on itself is sealed in liquid-tight fashion around its edges to define a compartment. The sealing means whereby the edges or marginal portions of the sheet are secured together may take any suitable form. Preferably, it is a layer of pressure sensitive adhesive. Alternatively, the sheet may be a plastics material and its edge regions may be shaped or molded to provide a "pop-in" rib and groove seal. To provide a labyrinthine type of seal at the edges, a multiple rib and groove arrangement may be adopted. In another arrangement, the sheet may be made of a foil material such as aluminum and the superposed edge regions rolled or folded together to provide a liquid seal. As another alternative, the sheet may be plastics but may have its ege regions laminated with metal foil so that a manual folding or rolling of the superposed edge regions can accomplish the desired sealing.

In use of such a device, an aperture is cut in the pad (and consequently through the adjacent portion of the sheet) of such a size as to be slightly larger than the wound, and the pad is applied so that the area surrounding the cut-out aperture adheres to that portion of the patient's skin which surrounds the wound, and the sheet is folded over on itself and sealed around the edges. A drain tube may be connected so that it is in communication with the interior of the compartment defined by the sheet which overlies and protects the wound.

One important advantage of such a device is that the cut-out can be made manually by hospital staff, e.g. with scissors, of a size to be appropriate to any particular wound and the sheet folded over, once the device is applied, to define a compartment whose interior is open to the wound and which receives any discharge from the wound. Wound management using such a device becomes more comfortable for the patient and a less labor-intensive task for nursing staff.

According to another aspect of the invention, there is provided a device for protecting a wound comprising a pad of skin-protective and skin-curative adhesive material which is secured to a sheet of liquid-impermeable material which constitutes one wall of a compartment. The compartment is defined by this wall and a container which makes a peripheral seal with the edge region of said wall. In use, an aperture of a size appropriate to the wound is cut through the pad and the sheet, the container is then sealed to the marginal region of the sheet to define a compartment for receiving discharge from the wound. A drain may be connected to the container, and the compartment may be shaped so that in its usual position when being worn by a patient, any discharge runs under gravity to a lower region to which is attached a drain tube.

The seal between the container and the said sheet may be of any convenient form. It could involve a groove at the marginal region of the sheet dimensioned to receive the edge of the container. It could involve a rib shaped coupling member having a thin, resilient, deflectible sealing strip on either the marginal region of the sheet or the edge of the container dimensioned to snap fit within a channel shaped coupling member as described by Steer et al. in British Pat. No. 1,571,657 or the coupling system described by Steer et al. in British Pat. Nos. 1,568,860 and 1,583,027.

BRIEF DESCRIPTION OF THE DRAWINGS

FIG. 1 is a perspective view of one example of device according to the invention;

FIG. 2 is a cross-section, with thicknesses exaggerated for clarity, on line A—A of FIG. 1 illustrating a cutout;

FIG. 3 is a view showing the device in place on a patient;

DETAILED DESCRIPTION OF THE INVENTION

Figure 4:
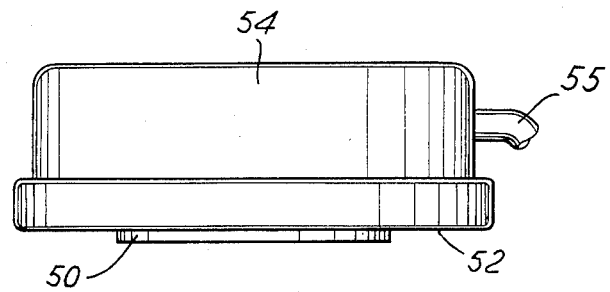
FIG. 4 is a side elevation of a second example of device according to the invention.

Referring firstly to FIGS. 1-3, a device for protecting a wound comprises a pad 10 secured to a foldable sheet 12. The pad 10 is a pad of adhesive material capable of securing the device to the body of a patient for several days. The pad 10 and the sheet 12 are secured together in any suitable manner. The sheet 12 has a larger area than the pad 10 and is foldable. The marginal regions 14 of the sheet 12 carry a pressure sensitive adhesive layer 16 which is covered by a protective strip 18. It will be seen from FIG. 1 that when the protective strips 18 are removed and the two parts of the sheet 12 folded together with pressure applied round the edges so that the sheet defines an enclosed compartment. Adhesive layer 16 can be coated directly onto marginal regions 14 or it can be a double-sided adhesive strip one side of which has been affixed to marginal regions 14 while the exposed adhesive surface is still covered by protective strip 18.

When a device according to the invention is to be used, an aperture 20 is cut out of the pad and the adjacent portion of the sheet. This aperture may be cut out with scissors. The aperture is of a size chosen to be slightly larger than the wound under consideration. One surface 22 of the pad 10 is then placed into contact with the patient on the area of skin surrounding the wound, and while this is not essential, it is convenient for this to be done before the two parts of the sheet are secured together around their marginal regions. It is thus possible to use the aperture 20 to properly locate the device on the wound.

An optional feature of the invention is also illustrated in FIG. 1. A drainage tube 24 is connected to the rim of a suitable hole 26 in the sheet 12 and a suitable tube coupling 28 is fixed to the distal end of the tube 24. A stopper 30 connected to a plastics strip 32 integral with the coupling 28 permits the bottom end of the coupling to be closed off.

In the embodiment of the invention shown in FIGS. 1 and 2, there could also be included an external peripheral zip fastener (sliding clasp fastener) to fasten the two sheets 12 together. It could be located outside the strip 14.

It will be realized that the device disclosed and illustrated is easily applied by nuring staff to a patient, and can readily be opened and closed to allow close visual examination of the wound, and permits any discharge from the wound to be drained. In addition, one size of device can be used for wounds of a wide range of dimensions.

Figure 5:
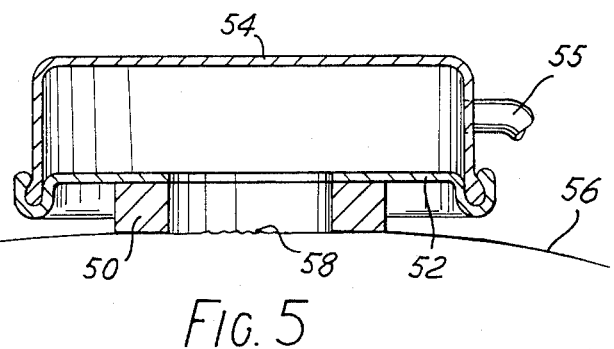
FIG. 5 is a cross-section of the device shown in FIG. 4 seen in position on a patient.

Another embodiment of the invention, incorporating similar principles, is illustrated in FIGS. 4 and 5 of the accompanying drawings. The device for wound management illustrated in FIGS. 4 and 5 comprises a pad 50 of skin-protective and skin-curative adhesive material which is fixed to a flat sheet of liquid-impermeable material of larger area than the pad. The sheet is indicated at 52. The sheet 52 is formed to define a marginal groove which extends completely around the periphery of the sheet 52. The marginal groove is constructed to snugly receive the edge of a container 54. In a preferred version of the invention, the sheet 52 and container 54 are of synthetic plastics material and the groove is constucted so that its width at entry is somewhat less than its width at deeper regions. With a synthetic plastics material of suitable resilience, a liquid-tight fit can be readily achieved between the sheet 52 and the container 54.

An optional feature of the embodiment of the invention shown in FIGS. 4 and 5 is the provision of drainage pipe 55 which is connected to the container 54, so that any discharge from the wound can be drained from the interior of the compartment defined by the sheet 52 and the container 54.

FIG. 5 illustrates the device in position on the body 56 of a patient, the open part of the wound being illustrated at 58. For clarity, the height of the pad is exaggerated; in a practical embodiment the pad 50 will be a thickness between about 0.1 and 0.5 inches, i.e. about 2.5 to 13 mm. While a snap fit groove construction has been disclosed for connecting the container 54 and the sheet 52, it will be appreciated that other known forms of sealing could be employed.

The skin-protective and skin-curative adhesive material employed as pad 10 or pad 50 can be any such adhesives that are commercially available. Particularly suitable adhesive compositions are pressure sensitive adhesive formulations that consist of a homogeneous blend of one or more water soluble or water swellable hydrocolloids dispersed in a viscous elastomeric substance such as polyisobutylene as disclosed by Chen in U.S. Pat. No. 3,339,546. Optionally, the adhesive composition can also include one or more cohesive strengthening agents as described by Chen et al. in U.S. Pat. No. 4,192,785 or one or more hydratable natural or synthetic polymers as described by Pawelchak et al. in U.S. Pat. No. 4,393,080. Prefeably, adhesive pad 10 or 50 includes a thin water insoluble polymeric film such as polyethylene that can be sealed directly to sheet 12 or sheet 52. Also, adhesive pad 10 or 50 can consist of a layer of such pressure sensitive skin-currative and skin-protective adhesive formulations bonded to a semi-open cell elastic or flexible foam as described by Pawelchak et al. in European Patent Application No. 92,999.

What is claimed is:

1. A device for protecting a wound comprising a paid of skin-protective and skin-curative adhesive material having secured thereto a foldable sheet of liquid impermeable material of larger area than the pad, marginal portions of said foldable sheet provided with a layer of pressure-sensitive adhesive, and said sheet folded over itself and sealed in liquid-tight fashion around its edges to define a compartment whereby the marginal portions can be manually pulled apart if desired.

2. A device according to claim 1 in which an aperture is cut through said pad and the portion of said sheet that is secured to said pad and said aperture is dimensioned to be slightly larger than the wound being treated.

3. A device according to claim 2 in which the marginal portion of one half of said foldable sheet has secured thereto an adhesive strip having adhesive on both of its surfaces, and the exposed surface of said adhesive strip has its adhesive covered by a removable protective strip.

4. A device according to claim 2 including a drain tube connected to said compartment so that it is in communication with the interior of said compartment.

* * * * *